(12) United States Patent
Inglese et al.

(10) Patent No.: US 8,712,228 B2
(45) Date of Patent: Apr. 29, 2014

(54) INTRAORAL CAMERA FOR DENTAL CHAIRS

(71) Applicants: Jean-Marc Inglese, Bussy Saint Georges (FR); Edward R. Shellard, Atlanta, GA (US)

(72) Inventors: Jean-Marc Inglese, Bussy Saint Georges (FR); Edward R. Shellard, Atlanta, GA (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/759,086

(22) Filed: Feb. 5, 2013

(65) Prior Publication Data
US 2013/0203010 A1    Aug. 8, 2013

Related U.S. Application Data

(60) Provisional application No. 61/595,806, filed on Feb. 7, 2012.

(51) Int. Cl.
*A61B 1/04*         (2006.01)

(52) U.S. Cl.
USPC .............................................. 396/16; 348/66

(58) Field of Classification Search
USPC ........................................ 396/14, 16; 348/66
See application file for complete search history.

(56) References Cited

U.S. PATENT DOCUMENTS

| | | | |
|---|---|---|---|
| 6,862,036 B2* | 3/2005 | Adair et al. | 348/76 |
| 2002/0118279 A1* | 8/2002 | Spoonhower et al. | 348/66 |
| 2004/0188625 A1 | 9/2004 | Schulze-Ganzlin | 250/370.09 |
| 2004/0218792 A1* | 11/2004 | Spoonhower et al. | 382/128 |
| 2013/0286174 A1* | 10/2013 | Urakabe | 348/66 |

FOREIGN PATENT DOCUMENTS

WO    WO2006008339 A1    5/2007

* cited by examiner

*Primary Examiner* — Clayton E Laballe
*Assistant Examiner* — Warren K Fenwick (57) ABSTRACT

An intraoral camera comprising: an imaging section for obtaining image data from a patient in a dental chair; a transmitter comprising a transmitter configured for both wired and wireless transmission of the obtained image data to a computer; and a power section including a cable that obtains power from the dental chair or a battery module within the camera.

17 Claims, 6 Drawing Sheets

INTRAORAL CAMERA FOR DENTAL CHAIRS

CROSS REFERENCE TO RELATED APPLICATIONS

This application claims priority to Provisional U.S. Patent Application Ser. No. 61/595,806, filed Feb. 7, 2012 in the names of Jean-Marc Inglese, et al., entitled INTRAORAL CAMERA FOR DENTAL CHAIRS, which is incorporated herein by reference in its entirety.

FIELD OF THE INVENTION

The invention relates generally to the field intraoral imaging and in particular to an intraoral camera adapted for use with the patient in the dental chair. More specifically, the invention relates to an intraoral digital camera that obtains its power from the dental chair and provides wireless transmission of images.

BACKGROUND OF THE INVENTION

Intraoral imaging is relied upon to provide useful information for the detection of caries and other dental conditions. A number of intraoral cameras have been developed for use by the dental practitioner or technologist, allowing an image of a patient's mouth to be readily obtained, displayed, and recorded.

One problem with conventional intraoral imaging solutions relates to providing suitable power for the imaging camera and its support circuitry and obtaining the image data in an efficient manner. Because of inherent difficulties in working around the patient and positioning the camera properly with a minimum of patient discomfort, using conventional arrangements of data and power cables can be awkward in practice and can limit the usability of the intra-oral imaging device.

A degree of portability is desirable for moving around the patient and for accessing portions of the mouth at suitable angles for imaging. A battery powered camera that provides wireless transmission has some advantages for portability and size. However, in order to provide video images at a sufficient rate for near "real-time" response, battery power must be maintained at high capacity, which may not be practical for some environments. Keeping a rechargeable battery well charged requires careful attention to detail on the part of the technician and is subject to human error or omission.

Thus, it can be appreciated that while there are some conventional solutions for providing power and obtaining data from an intraoral camera, there is a need for solutions that are suited to the dental office environment.

SUMMARY OF THE INVENTION

An object of the present invention is to address the need for an improved intraoral imaging apparatus for the dental office environment. Embodiments of the present invention provide novel and convenient methods for providing power to an intraoral camera that is particularly well suited for use in an examination setting. Embodiments of the present invention take advantage of support power available through the dental chair and its associated utilities and adapt this power to meet the particular requirements of the intraoral camera.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an intraoral camera comprising: an imaging section for obtaining image data from a patient in a dental chair; a transmitter comprising a transmitter configured for both wired and wireless transmission of the obtained image data to a computer; and a power section that obtains power from either a power cable connected to the dental chair or a battery module within the camera.

According to an alternate aspect of the invention, there is provided a method for obtaining an image at an intraoral camera, the method comprising: sensing whether a power source for the intraoral camera is provided from a battery that is coupled to the intraoral camera or from a power outlet on a dental chair; sensing whether or not there is data cable connection to a computer through a port on the dental chair; obtaining image data at the intraoral camera; and transmitting the obtained image data to the computer according to the sensed power source, using wireless transmission when the power source is from the power outlet and using the data cable connection when the power source is from the battery.

According to an alternate aspect of the invention, there is provided a method for obtaining an image at an intraoral camera, the method comprising:

sensing whether a power source for the intraoral camera is provided from a battery that is coupled to the intraoral camera or from a power outlet on a dental chair; sensing whether or not there is data cable connection to a computer through a port on the dental chair; obtaining image data at the intraoral camera; and transmitting the obtained image data to a computer according to the sensed power source, using wireless transmission when the power source is from the battery and using the data cable connection when the power source is from the power outlet.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Figure 1:
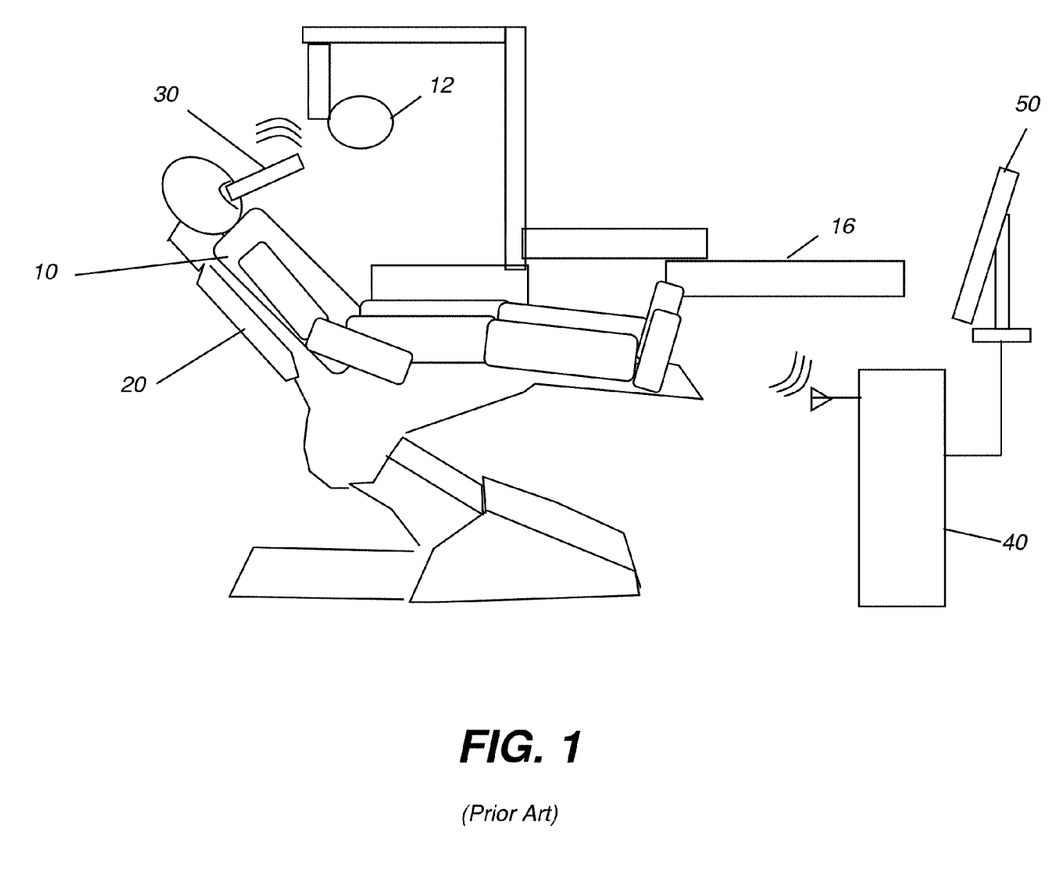
FIG. 1 shows an intraoral camera providing wireless communication with a computer in a dental examination environment.

FIG. 1 shows an intraoral camera 30 providing wireless communication with a computer in a dental examination environment. Intraoral camera 30 is used to image a patient 10 in a dental chair 20. Image data is transmitted in a wireless manner to a computer 40 that is typically positioned in the near proximity of dental chair 20, with a display 50 for viewing the resulting video image that is obtained. Dental chair 20 is understood to comprise not only the seat on which the patient is positioned but typically also includes a number of support structures, such as a movable table 16, and a light 12, for example, and is often provided with a number of built-in electrical and plumbing components that serve in the examination process. A variable number of direct current (DC) output voltages, provided from circuitry that is part of dental chair 20, can be available in different dental chair 20 embodiments.

Figure 2:
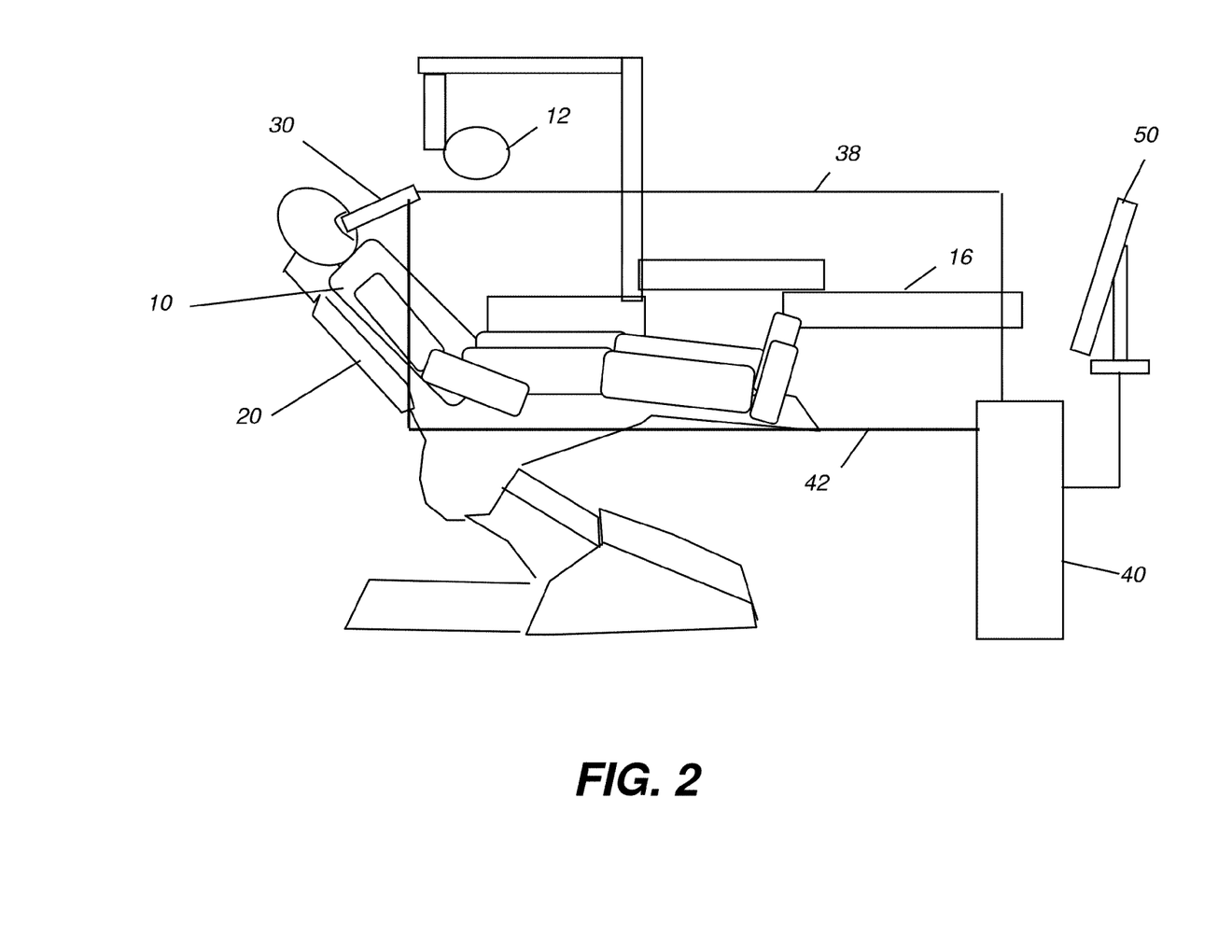
FIG. 2 shows an intraoral camera providing wired communication with the computer, wherein the computer power is used for camera circuitry.

Intraoral camera 30 includes source power and a transmission channel for providing the image data that it obtains. The schematic block diagram of FIG. 2 shows intraoral camera 30 providing wired communication with the computer by means of a data wire 38. For this embodiment, camera power is provided from computer 40 using a power cable 42. As was noted previously in the background section, using a camera with attached cables can prove awkward in the dental imaging environment.

Figure 3:
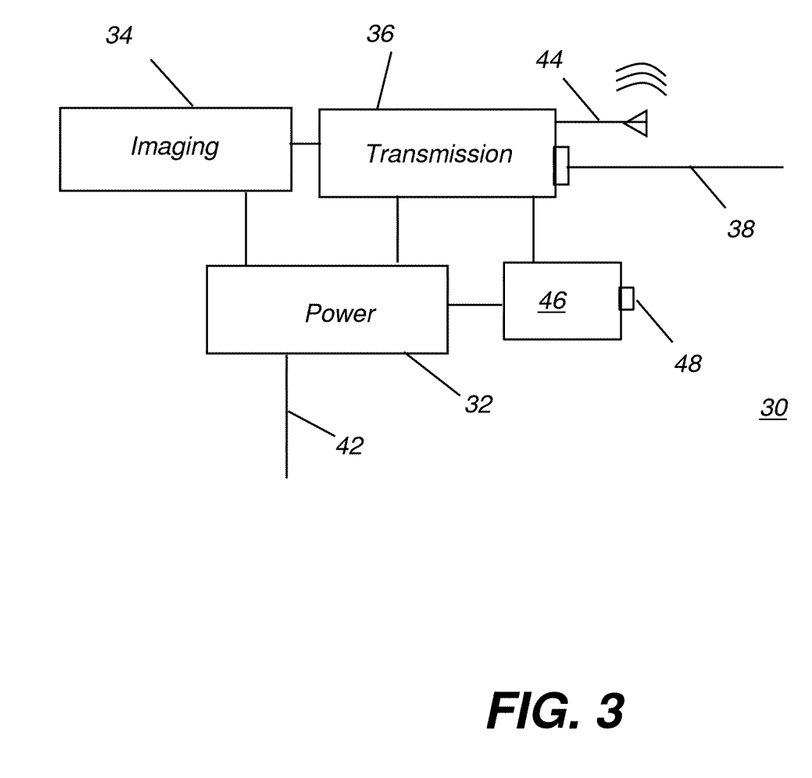
FIG. 3 is a schematic block diagram that shows intraoral camera circuitry allowing wired or wireless transmission.

The schematic block diagram of FIG. 3 shows intraoral camera circuitry for either wired or wireless transmission. An imaging section 34 includes the optical and electronic components needed to obtain the image and to form image data. Imaging section 34 typically includes components for illumination of the tooth area, lenses and other support optics for directing light to a CCD (charge-coupled device) or CMOS (complementary metal-oxide semiconductor) sensor array that generates the image data, and memory circuitry for buffering or otherwise temporarily storing the obtained image content. Image data can be still image data frames or data in video format. Transmitter 36 includes components that format the image data for transmission and send the data over the transmission link. The transmitter is switchable to transmit data either wirelessly using an antenna 44 or in wired mode, using data wire 38. Data wire 38 may be a standard USB (Universal Serial Bus) cable, for example, or some other cable type, such as an Ethernet cable. According to an embodiment of the present invention, transmitter 36 is capable of sensing whether or not wired connection is provided by data wire 38 and of switching its mode of transmission accordingly. Where wired connection is not provided, transmitter 36 is configured to transmit the data in wireless form. Wireless data transmission can use any of a number of transmission formats or protocols, including WiFi, Bluetooth, RF, and other transmission types. In general, wireless transmission can require more power than wired digital data transmission; this factor is taken into consideration for determining the amount of useful battery power in embodiments of the present invention.

Still referring to FIG. 3, a power module 32 provides the needed source power for operation of imaging section 34 and transmitter 36. Power module 32 may be self-contained, providing a rechargeable or non-rechargeable battery. Optionally, power module 32 may provide or condition and redirect power from some other source in the examination area, as described in more detail subsequently. A power monitor 46, associated with or integrated as part of power module 32, checks battery power and provides a power status signal that is indicative of the relative amount of battery power available. The power status signal is used to determine whether or not power from an optional power cable 42 should be used.

According to an embodiment of the present invention, the signal provided from monitor 46 is used to provide an audible or visual indicator 48 of battery power status on the handle of camera 30. According to an alternate embodiment of the present invention, the power status signal is transmitted wirelessly to computer 40 (FIG. 2). Upon receipt of the power status signal, computer 40 determines the status of battery charge, whether acceptable, low, or unusable and displays an advisory or warning message on display 50 related to the need to replace or recharge the battery; or, optionally, recommending connection of power cable 42 to camera 30 or the use of the wired communication cable, data wire 38 (FIG. 3). According to another alternate embodiment of the present invention, display 50 shows a timing icon that indicates an estimated amount of time available for camera 30 operation based on the battery charge level. Different estimates can be provided for different modes of transmission, wired and wireless.

According to an embodiment of the present invention, connection of power cable 42 to camera 30 performs a dual function: operating the camera while also recharging power module 32. This configuration enables the practitioner to use battery power only when necessary, such as when use of power cable 42 may be awkward due to patient positioning or the use of other devices or equipment during patient treatment.

Figure 4:
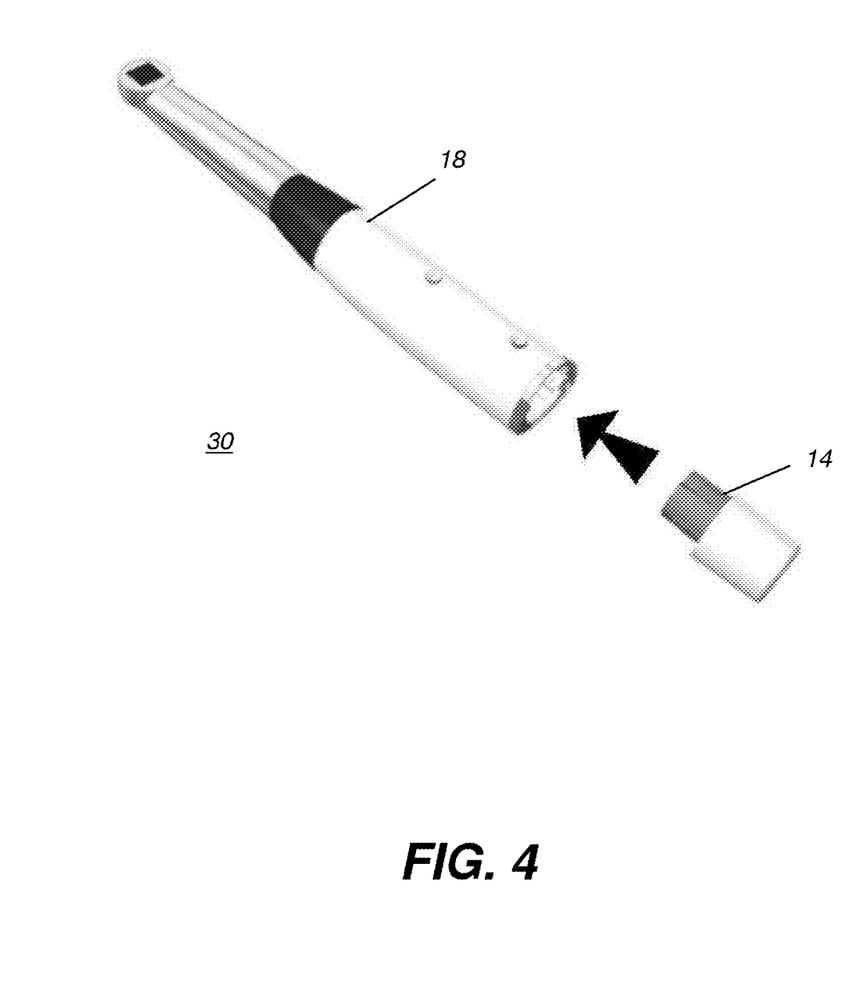
FIG. 4 shows an intraoral camera that accepts a battery power module.

FIG. 4 shows an intraoral camera 30 that accepts a battery power module 14. When battery power module 14 is installed at the base of a handpiece 18, intraoral camera 30 is automatically placed in wireless transmission mode. According to one embodiment of the present invention, battery power module 14 is a rechargeable unit, recharged using a docking station or similar device (not shown) to maintain the charge of a battery or of a complete battery power module 14 when not in use. In an alternate embodiment, battery power module 14 accepts a non-rechargeable battery.

Figure 5:
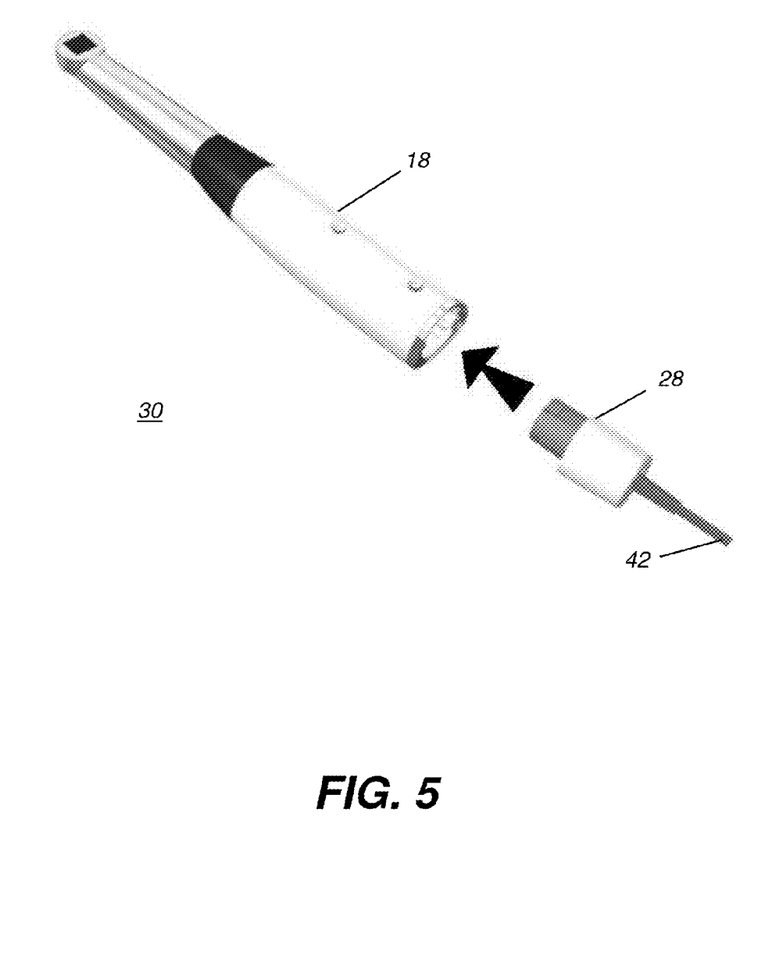
FIG. 5 shows an intraoral camera that accepts a wired power module.

FIG. 5 shows intraoral camera 30 using a wired power module 28. In this embodiment, power cable 42 provides power from a suitable source that is within the examination area.

Figure 6:
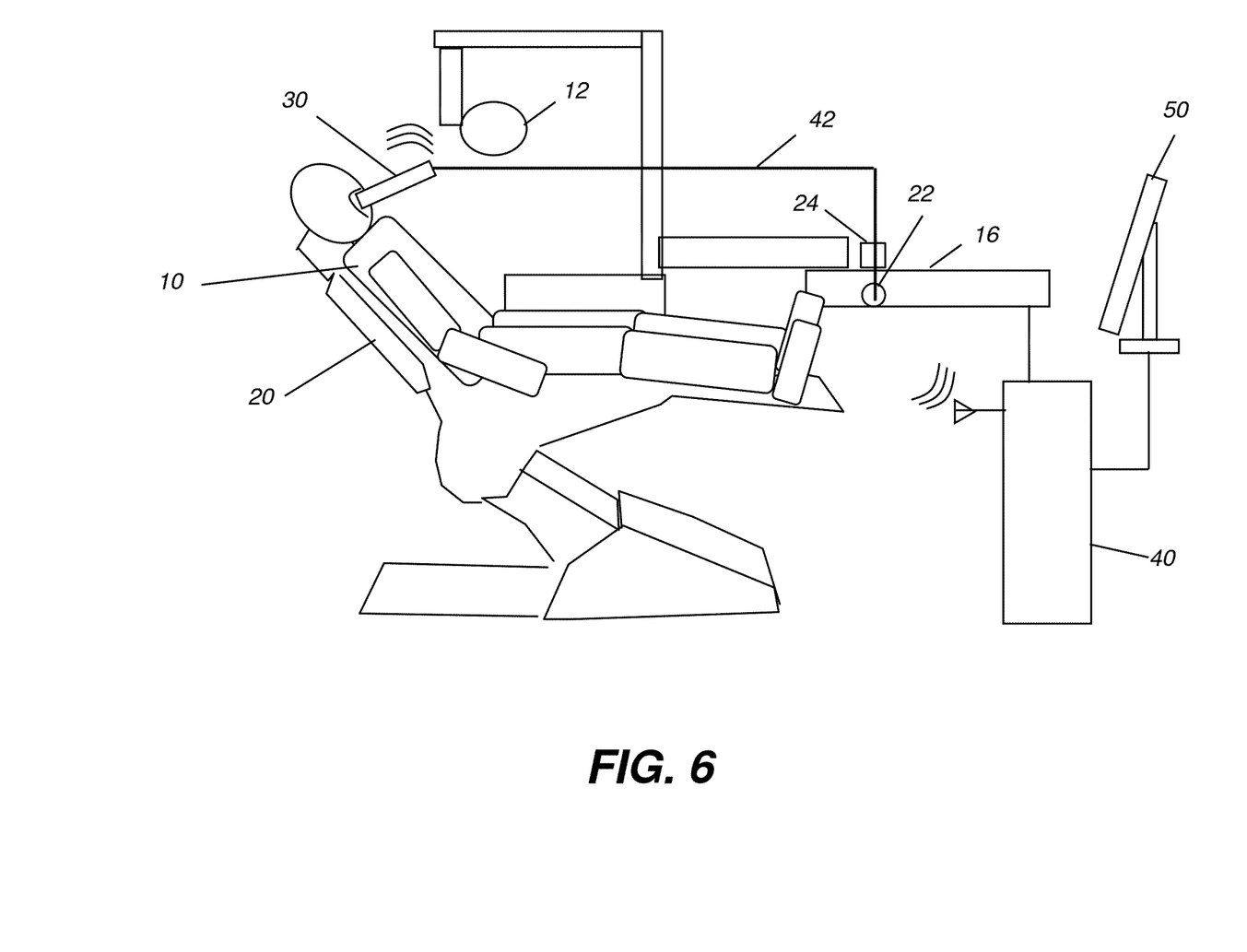
FIG. 6 shows an intraoral camera providing wireless communication with a computer and obtaining source power from the dental chair.

The schematic block diagram of FIG. 6 shows intraoral camera 30 providing wireless communication with a computer and obtaining source power from a power outlet or connection port 22 on dental chair 20. This embodiment takes advantage of advanced capabilities of dental chairs 20, including power connection ports 22 that provide power outlets that can be used for providing source power to various dental instruments. An optional adapter 24 is provided to condition the power provided from port 22 for use by camera 30, such as by reducing the voltage level or changing current characteristics from AC to DC, for example. Adapter 24 may provide filtering, voltage level adjustment, power isolation, fusing, connector adaptation, or other features needed to condition the power from the power outlet or port 22 connection for use by intraoral camera 30.

According to an optional embodiment of the present invention, the intraoral camera 30 tests battery power module 14 for power prior to initiating wireless transmission. This tests battery power module 14 for a threshold voltage or other value indicative of battery power, in order to determine whether or not there is sufficient power for successful acquisition and wireless transmission of image data. This can include, for example, predetermined estimates of the amount of power that would be needed to provide a video imaging sequence of a given duration, such as 3 or 4 minutes of sustained video acquisition and wireless transmission. A different power estimate may be provided for wired transmission. Where power is detected below the threshold measurement, the operator is alerted to a low-battery condition, such as by an audible beeping or visual indicator, or indicated by a message on display 50, for example. With power below a predetermined threshold voltage or current value, the operator may be advised or instructed to either use wired power or use a wired data transmission channel. Alternately, the operator may be advised to install a new or recharged battery in camera 30. The determination of whether or not there is sufficient battery power for acquisition and wireless transmission of data is based on estimates of power usage under standard operating conditions.

According to an embodiment of the present invention, camera 30 switches between wireless and wired transmission over data wire 38 as needed, such as when battery power drops below a threshold value during operation. Alternately, camera 30 switches to wired transmission over data wire 38 when wireless transmission is operating poorly, such as when excessive retries are required for sending data over the wireless channel.

According to an embodiment of the present invention, power cable 42 is a USB cable, or cable with a connector type that is compatible with the standard USB profile, but may provide only the power output, provided on suitable connector pins. In an alternate embodiment of the present invention, power cable 42 may provide data connectors that are not used for obtaining data from the camera 30, but that allow cable 42 to be used for one or more alternate devices. Computer 40 may also be in signal communication with the dental chair 20, such as to control aspects of operation or to obtain data from various dental instruments or devices, for example.

According to another alternate embodiment of the present invention, intraoral camera 30 transmission logic (at transmitter 36 in FIG. 3, for example) senses where the power is coming from (for example, whether power module 32 has a battery or connects to port 22 for power as in FIG. 6) and sets its transmission mode accordingly. Sensing of the power source can be done in a number of ways, including by mechanical detection of battery presence, sensing battery voltage, sensing an auxiliary signal, or sensing a ground connection provided through a cable, for example. Thus, for example, wireless transmission is used as the default transmission method; if, however, data wire 38 as in FIG. 2 is provided and connected to computer 40, camera 30 attempts to send data through this wired connection. Methods for sensing whether or not a data cable communication link exists between two devices are straightforward and are familiar to those skilled in the data communication arts.

It is noted that computer 40, and optionally display 50, may be more closely integrated with dental chair 20 so that some or all of the image transmission, processing, and display functions are performed by processing circuitry at dental chair 20. This type of embodiment may be suited, for example, with more advanced dental chair designs. Suitable connection ports 22 for camera 30 connection may be located at various positions on dental chair 20, including ports at positions nearer to or behind the patient's head, for example.

Computer 40 can be any of a number of types of computer or processor and the logic processes for determining camera 30 response due to power level or detection of wireless communication problems can be performed by external computer 40 or by a processor within the camera. Consistent with an embodiment of the present invention, a computer executes a program with stored instructions that perform on image data accessed from an electronic memory. As can be appreciated by those skilled in the image acquisition and processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected by way of the internet or other communication medium. Those skilled in the art will readily recognize that the equivalent of such a computer program product may also be constructed in hardware.

It will be understood that the computer program product that implements portions of the present invention may make use of various sensing and data analysis algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An intraoral camera comprising:
   an imaging section for obtaining image data from a patient in a dental chair;
   a transmitter configured for both wired and wireless transmission of the obtained image data to a computer; and
   a power section that obtains power from either a power cable connected to the dental chair or a battery module within the camera.

2. The intraoral camera of claim 1 further comprising an adapter for conditioning power from the dental chair.

3. The intraoral camera of claim 1 wherein the battery module is rechargeable through the power cable.

4. The intraoral camera of claim 1 wherein the computer is in signal communication with the dental chair.

5. The intraoral camera of claim 1 wherein the transmitter senses the presence of a data connection to the computer.

6. The intraoral camera of claim 1 wherein the image data is video image data.

7. The intraoral camera of claim 1 further comprising a power section monitor that provides a signal that is indicative of battery power in the battery module.

8. The intraoral camera of claim 1 wherein the transmitter is configured to switch between either wired transmission over a data cable or wireless transmission of the obtained image data, according to the signal from the power section monitor.

9. The intraoral camera of claim 1 wherein the transmitter is configured to switch from wired to wireless transmission when the battery power falls below a threshold value.

10. The intraoral camera of claim 1 wherein the transmitter is configured to switch from wired to wireless transmission when the data cable is removed.

11. A method for obtaining an image at an intraoral camera, comprising:
    sensing whether a power source for the intraoral camera is provided from a battery that is coupled to the intraoral camera or from a power outlet on a dental chair;
    sensing whether or not there is data cable connection to a computer through a port on the dental chair;
    obtaining image data at the intraoral camera; and
    transmitting the obtained image data to the computer according to the sensed power source, using wireless transmission when the power source is from the power outlet and using the data cable connection when the power source is from the battery.

12. The method of claim 11 wherein sensing the power source comprises sensing a mechanical connection or sensing a voltage or current level.

13. The method of claim 11 further comprising displaying information about a power level of the battery on a display screen that is associated with the computer.

14. A method for obtaining an image at an intraoral camera, comprising:
    sensing whether a power source for the intraoral camera is provided from a battery that is coupled to the intraoral camera or from a power outlet on a dental chair;
    sensing whether or not there is data cable connection to a computer through a port on the dental chair;
    obtaining image data at the intraoral camera; and
    transmitting the obtained image data to a computer according to the sensed power source, using wireless transmission when the power source is from the battery and using the data cable connection when the power source is from the power outlet.

15. The method of claim 14 further comprising testing the wireless transmission between the intraoral camera and the computer.

16. The method of claim 14 further comprising determining that power from the battery meets or exceeds a threshold value prior to transmitting the obtained image data.

17. The method of claim 14 wherein transmitting the obtained image data further comprises switching to wireless transmission when the data cable connection is removed.

* * * * *